(12) United States Patent
Sereboff et al.

(10) Patent No.: US 8,731,632 B1
(45) Date of Patent: May 20, 2014

(54) ELECTROCARDIOGRAM DEVICE

(76) Inventors: Joel L. Sereboff, Owings Mills, MD (US); Kevin Barnes, Westminster, MD (US)

( * ) Notice: Subject to any disclaimer, the term of this patent is extended or adjusted under 35 U.S.C. 154(b) by 208 days.

(21) Appl. No.: 13/212,736

(22) Filed: Aug. 18, 2011

(51) Int. Cl.
*A61B 5/0408* (2006.01)
(52) U.S. Cl.
USPC ............ 600/382; 600/390; 600/393; 600/509
(58) Field of Classification Search
USPC .................................. 600/382, 390, 393, 509
See application file for complete search history.

(56) References Cited

U.S. PATENT DOCUMENTS

| | | | |
|---|---|---|---|
| 3,888,240 A * | 6/1975 | Reinhold et al. ............... | 600/390 |
| 4,121,575 A | 10/1978 | Mills et al. | |
| 4,202,344 A * | 5/1980 | Mills et al. .................... | 600/382 |
| 4,233,987 A * | 11/1980 | Feingold ....................... | 600/382 |
| 4,583,549 A | 4/1986 | Manoli | |
| 4,763,660 A * | 8/1988 | Kroll et al. .................... | 600/391 |
| 5,027,824 A | 7/1991 | Dougherty et al. | |
| 5,042,481 A * | 8/1991 | Suzuki et al. ................. | 600/393 |
| 5,085,224 A | 2/1992 | Galen et al. | |
| 5,307,818 A * | 5/1994 | Segalowitz .................... | 600/509 |
| 5,685,303 A * | 11/1997 | Rollman et al. ............... | 600/390 |
| 5,813,979 A * | 9/1998 | Wolfer .......................... | 600/373 |
| 6,076,003 A * | 6/2000 | Rogel ............................ | 600/390 |
| 6,282,439 B1 | 8/2001 | Ruha | |
| 6,360,119 B1 | 3/2002 | Roberts | |
| 6,400,975 B1 * | 6/2002 | McFee .......................... | 600/372 |
| 6,416,471 B1 | 7/2002 | Kumar et al. | |
| 6,611,705 B2 | 8/2003 | Hopman et al. | |
| 7,160,253 B2 | 1/2007 | Nissila | |
| 7,272,428 B2 | 9/2007 | Hopman et al. | |
| 2003/0045804 A1 | 3/2003 | Brodnick | |
| 2005/0049515 A1 | 3/2005 | Misczynski et al. | |
| 2005/0113661 A1 | 5/2005 | Nazeri et al. | |
| 2006/0149156 A1 | 7/2006 | Cochran et al. | |
| 2006/0264767 A1 | 11/2006 | Shennib | |
| 2006/0282001 A1 | 12/2006 | Noel et al. | |
| 2007/0093719 A1 | 4/2007 | Nichols, Jr. et al. | |
| 2007/0106133 A1 | 5/2007 | Satchwell et al. | |
| 2007/0149886 A1 | 6/2007 | Kohls | |
| 2008/0015454 A1 | 1/2008 | Gal | |
| 2008/0064970 A1 | 3/2008 | Montplaisir | |
| 2009/0099469 A1 | 4/2009 | Flores | |
| 2010/0042008 A1 | 2/2010 | Amitai et al. | |
| 2011/0270100 A1 * | 11/2011 | Chang ........................... | 600/509 |

OTHER PUBLICATIONS

"New vest to assist in heart diagnoses", Mar. 25, 2002, obtained from the Internet on Oct. 26, 2010 at http://articles.baltimoresun.com/2002-03-25/news/0203250207_1_meridian—vest-heart, 1 page.

(Continued)

*Primary Examiner* — Lee S Cohen
(74) *Attorney, Agent, or Firm* — Ditthavong Mori & Steiner, P.C.

(57) ABSTRACT

An electrocardiogram device, and a corresponding method of administering an electrocardiogram, includes a housing that is placed over a patient's chest, a plurality of electrodes mounted on the housing that align with precordial positions, a conductive gel pad detachably affixed on the housing between the electrodes and the patient's body, and an attachment mechanism for attaching the electrocardiogram device to the patient's chest. The electrocardiogram device of the present invention is suitable for portable or remote testing, and it ensures proper placement of the electrodes for accurate and consistent results.

21 Claims, 6 Drawing Sheets

(56) References Cited

OTHER PUBLICATIONS

G. Ostrovsky, "Visi Mobile System for Real Time Wireless In-Hospital Vital Signs Monitoring (Video)", <http://medgadget.com/2012/08/visi-mobile-system-for-real-time-wireless-in-hospital-vital-signs-monitoring-video.html>.

LifeSync Corporation, "The LifeSync Wireless ECG System", Technology and Services Section, Emergency Mwedical, vol. 4, Issue 1, Touch Briefings 2008, <http://www.lifesynccorp.com/assets/pdfs/Lifesync_Tech_hr%5B1%5D.pdf>.

NASA Johnson Space Center et al., "Wireless Self-Acquisition of 12-Lead ECG Via Android Smart Phone", <http://www.nasa.gov/pd/644144main_schlegel.pdf>.

\* cited by examiner

ELECTROCARDIOGRAM DEVICE

BACKGROUND OF THE INVENTION

1. Field of the Invention

The present invention relates generally to the field of medical data gathering devices, and, more particularly, to an electrocardiogram ("ECG" or "EKG") device and method of use including features that facilitate accurate placement of the device on a patient.

2. Discussion of the Background Art

An ECG is a medical diagnostic test that measures electrical activity of the heart. The results of an ECG reflect the direction of electrical current flow through the heart, as well as the magnitude of the heart muscle that is depolarized. The ECG provides a noninvasive way for health care professionals to diagnose arrhythmias and conduction irregularities of the heart.

It is well known to perform an ECG by placing electrodes at specific locations on the body to capture tracings of the heart's electrical activity. Electrodes usually consist of a conducting gel embedded in an electro-conductive material, to which cables are clipped on. Each lead, or output from a pair of electrodes, records the electrical activity resulting from a depolarization and a repolarization of the heart. ECGs vary in the number of electrodes and leads, but they all provide a summation of the information recorded from each lead. In a traditional twelve lead ECG, ten adhesive electrode pads are attached to the body, and each electrode is connected to a wire that leads to a monitor. The ten electrodes of the twelve lead ECG consist of six precordial electrodes, which are placed above the heart, and four limb electrodes, one on each arm and each leg. The six precordial leads are labeled as V leads and are numbered V1-V6. The lead connected to the right leg is a neutral lead. There also exist, for example, three and five lead ECGs.

In order to obtain quality data, it is important for the electrodes to be placed at the correct locations on the body and with good contact with the skin. In the ECGs that are currently employed, the electrodes are often inconsistently or inaccurately positioned on the body. The proper positioning of the precordial electrodes, in particular, is very specific. The precordial electrodes are positioned at various intercostal spaces of the rib cage. Therefore, one must exercise great care to ensure proper positioning. Furthermore, the electrodes need to be placed at the same positions each time an ECG is administered so that ECG results for a particular patient may be compared to the patient's past results to look for changes in the heart's activity. Even slight differences in electrode position can lead to discrepancies in ECG results, so consistent placement is essential to ensure accurate comparison. Particularly in busy physicians' offices, technicians and nurses administering ECGs are sometimes rushed and do not practice the necessary level of care and accuracy in electrode positioning. Therefore, there is a need in the art for a way to ensure accurate and consistent positioning of electrodes. Other disadvantages of the current art are that electrode wires easily become tangled, which is burdensome for those administering ECGs. Additionally, many ECGs require the use of adhesive pads which may irritate patients' skin or cause particular discomfort to patients with hairy body surfaces.

There also remains a need in the art for portable ECG devices that are as effective as those that are stationarily located at hospitals and physicians' offices. There is a need for small, portable ECG devices that can be self-administered in the comfort of a patient's home or by emergency personnel in an ambulance or at the site of an accident. Particularly when the patient or care giver is not trained in administering ECGs, it is important to ensure that the device is easy to use and that the user accurately positions the electrodes.

SUMMARY OF THE INVENTION

Accordingly, it is a primary object of the present invention to overcome the above mentioned problems and disadvantages of prior art electrocardiogram devices.

It is another, more specific, object of the present invention to provide an electrocardiogram device that facilitates accurate and consistent electrode positioning, even by users who are not trained to use electrocardiograms or emergency personnel in unconventional settings.

It is a further object of the present invention to provide an electrocardiogram device that is easily transportable and conveniently storable.

The present invention is generally characterized in an electrocardiogram device with a first side configured for placement adjacent to a chest of a patient, a plurality of electrodes mounted on the first side of the housing at locations that align with precordial positions, a conductive gel pad detachably affixed to the housing and extending over two or more of the plurality of electrodes so as to be disposed between the electrodes and the patient's chest when the electrocardiogram assembly is attached to the patient, and an attachment mechanism extending from the housing for attaching the electrocardiogram device to the patient's chest. In a preferred embodiment, an elastic member is disposed on the housing to place the gel pad in compression between the electrodes and the patient's chest. The electrocardiogram device also includes limb electrode wires that are connected to the housing and are retractable and lockable. The electrocardiogram device has a power supply, a processor, and a memory disposed within the housing, and it can include a wireless communication module for receiving test results from the processor and transmitting results to a remote device.

Another aspect of the present invention, the electrocardiogram device includes an electrode positioner having a distal tip extendible from a first position relative to the housing to a second position spaced from the housing, where the distal tip is spaced from the housing in the second position a distance corresponding to a desired spacing between said electrodes and the patient's jugular notch. In a preferred embodiment, the distal tip is extendible to a plurality of positions corresponding to desired spacings for patients of different body sizes. For example, the positions can correspond to child, male and female spacings.

Another aspect of the present invention is generally characterized in a method of administering an electrocardiogram including the steps of attaching a conductive gel pad to the housing so that at least a portion of the gel pad covers the electrodes, positioning the housing adjacent a chest of a patient so that at least some of the electrodes are aligned with precordial positions and the gel pad is disposed between the housing and the patient, securing the housing to the patient such that the gel pad is placed in compression between the housing and the chest of the patient, administering an electrocardiogram using the housing and the gel pad, and removing the gel pad from the housing.

The above and other features and advantages of the present invention will be further understood from the following description of the preferred embodiments thereof, taken in conjunction with the accompanying drawings wherein like reference numerals denote like parts.

DETAILED DESCRIPTION OF THE PREFERRED EMBODIMENTS

An electrocardiogram device 100 according to the present invention, as illustrated in FIGS. 1-5, includes a housing 102, a plurality of electrodes 104 mounted on the housing, a conductive gel pad 106 detachably affixed to the housing, an electrode positioner 108 and an attachment mechanism 110 extending from the housing. The design of the electrocardiogram device makes it suitable for use as a portable testing device that enables patients or care givers to accurately and conveniently administer an electrocardiogram.

Figure 1:
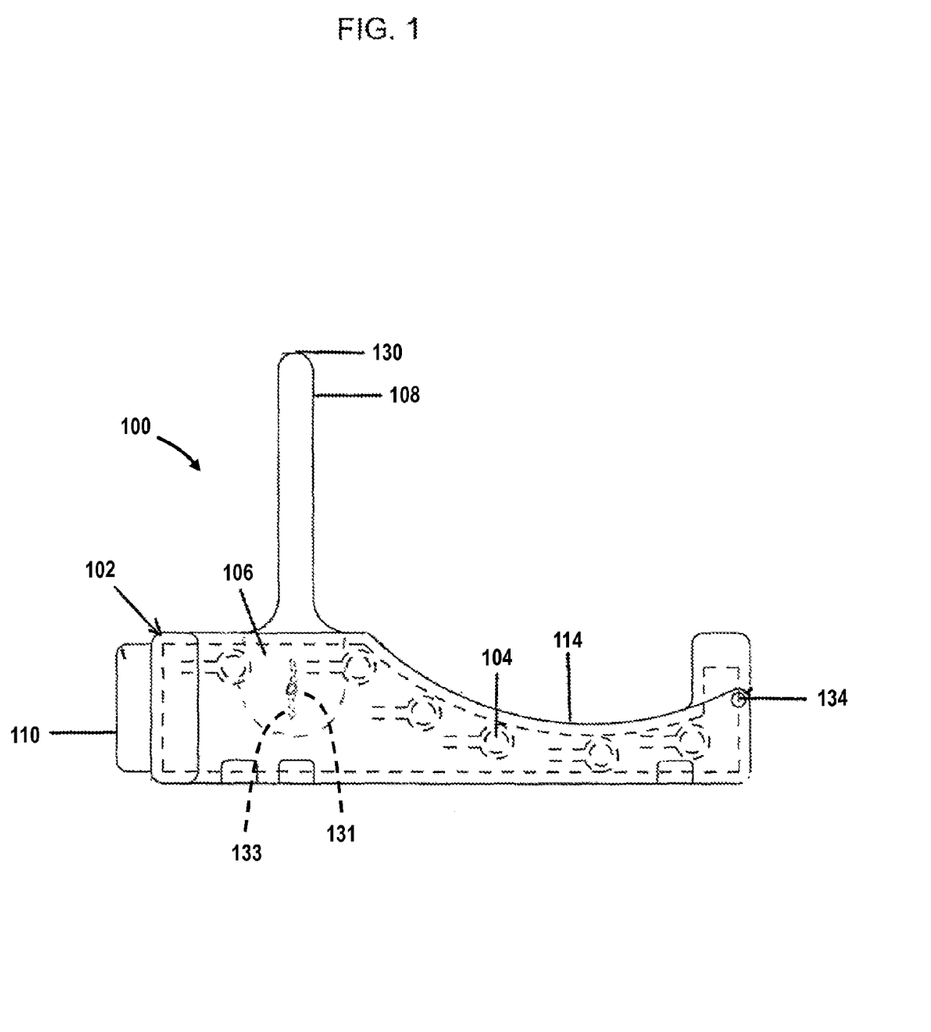
FIG. 1 is a top view of a housing for an electrocardiogram device according to an embodiment of the present invention.
Figure 2:
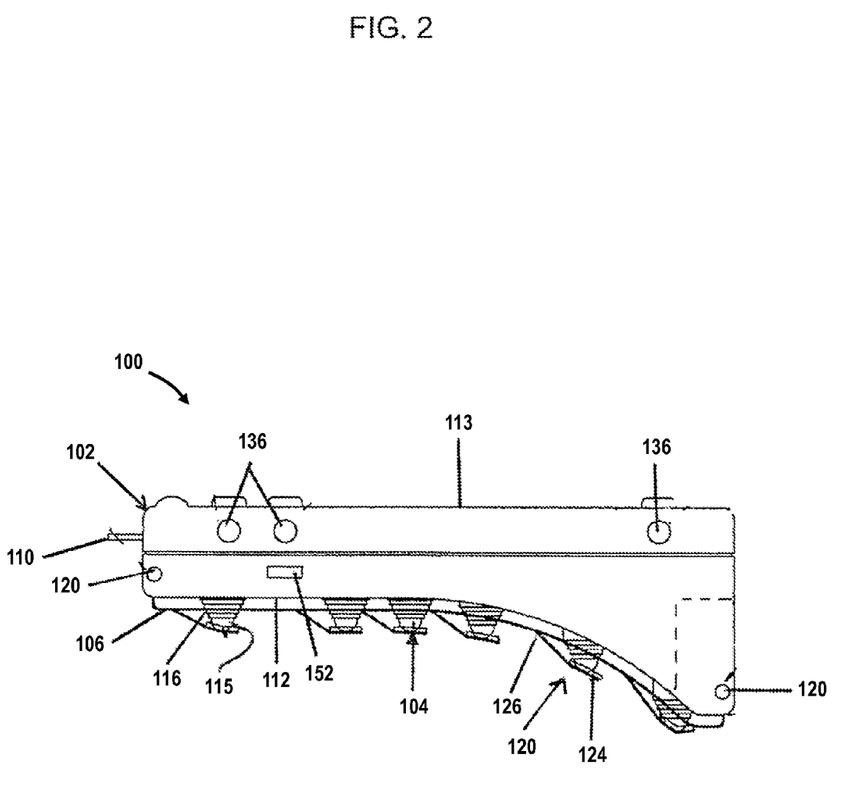
FIG. 2 is a side view of an electrocardiogram device, according to an embodiment of the present invention, showing a housing, a gel pad apparatus, retracted limb electrode wires, and a plurality of electrodes.

FIGS. 1 and 2 show front and bottom views of a device housing 102 according to an embodiment of the present invention. As will be described below, the major components of the electrocardiogram device are contained within the housing 102. The housing includes a first side 112 contoured to conform to the shape of a patient's chest and a second side 113 that is generally flat. As such, when viewed from the side, the housing 102 is generally wedge shaped. Upper and lower edges of the housing 102 are generally parallel except for a curved cutaway 114 along the upper edge. The curved cutaway 114 provides increased fit and comfort because the housing is not placed directly over the pectoral muscles or breast tissue. The length and width of the housing 102 should be sufficient for the housing to cover precordial positions on the chest. The housing is preferably approximately 8-10 inches long and 2-3 inches wide. The housing may be formed of a generally rigid plastic or metal material. Alternatively, the housing may be formed of a non-rigid or flexible material so that it bends easily and conforms well to the contours of patients' chests. This non-rigid material can be a urethane or a rubber-like material. The housing made of a non-rigid material possesses benefits such as added comfort to the patient and that it is less fragile than a conventional, rigid electrocardiogram device.

A plurality of electrodes 104 is mounted on the first side 112 of the housing 102. The electrodes 104 are mounted on the housing 102 so that they align with precordial positions over the patient's heart. A standard electrocardiogram, for example, consists of six precordial electrodes at positions V1-V6. Therefore, in a preferred embodiment, six electrodes 104 are mounted on the first side of the housing 112 to align with precordial positions V1-V6. That is, when the electrode positioner 108 is used to properly position the housing 102 adjacent to the patient's chest, the precordial electrodes align properly with precordial electrocardiogram positions over the patient's heart. In this embodiment, the electrodes 104 are hemi-spherically shaped, conductive contacts 115 mounted on frusto-conical collars 116. Referring to FIG. 2, the precordial electrodes 104 may be spring-loaded, e.g., by configuring the electrode collars 116 to include a spring-loaded bellows. The precordial electrodes 104 may optionally be movably disposed for storage inside the housing 102 (or the collars 116) when not in use so as to avoid damage to the electrodes during transport or storage of the electrocardiogram device 100.

Conductive gel pad 106 is detachably affixed to the first side 112 of the housing 102, extending over two or more, and preferably all, of the plurality of electrodes 104. As can be seen from FIGS. 1 and 2, the conductive gel pad 106 is disposed between the electrodes 104 and the patient's chest when the electrocardiogram housing 102 is attached to the patient. The gel pad 106 is attached to the housing 102 so that it stays in the proper position when in use. An attachment means 110 can include tab portions on the gel pad 106 that are configured to be received within openings at both ends of the housing. A lock mechanism 120 at each of the openings may contain a movable member that retains the tab portions of the gel pad 106 in the openings when the lock mechanism is engaged or locked. This retention constitutes a locked position of the gel pad 106 on the housing 102. The lock mechanism 120 may be disengaged or unlocked to permit removal of the tab portions from the openings in the housing to create an unlocked position in which the pad may be removed.

Figure 3:
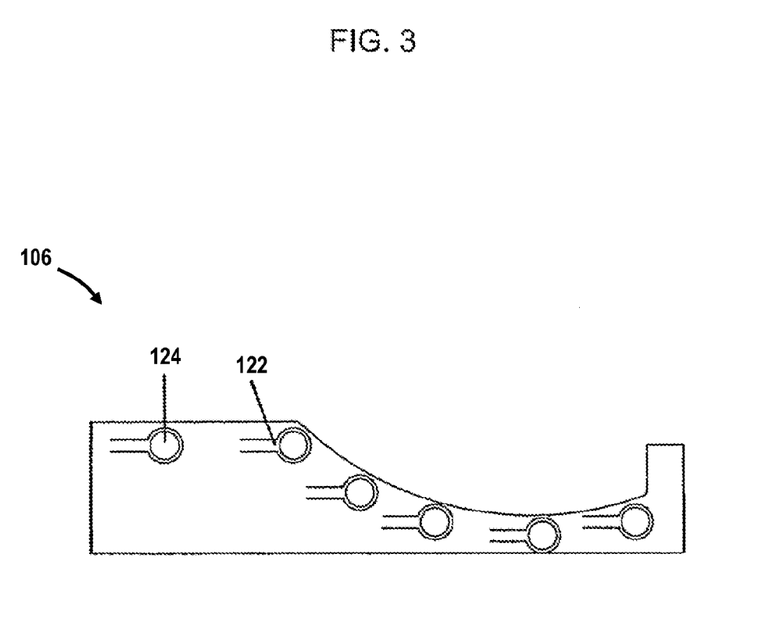
FIG. 3 is a top view of a conductive gel pad for use in an electrocardiogram device according to an embodiment of the present invention.
Figure 4:
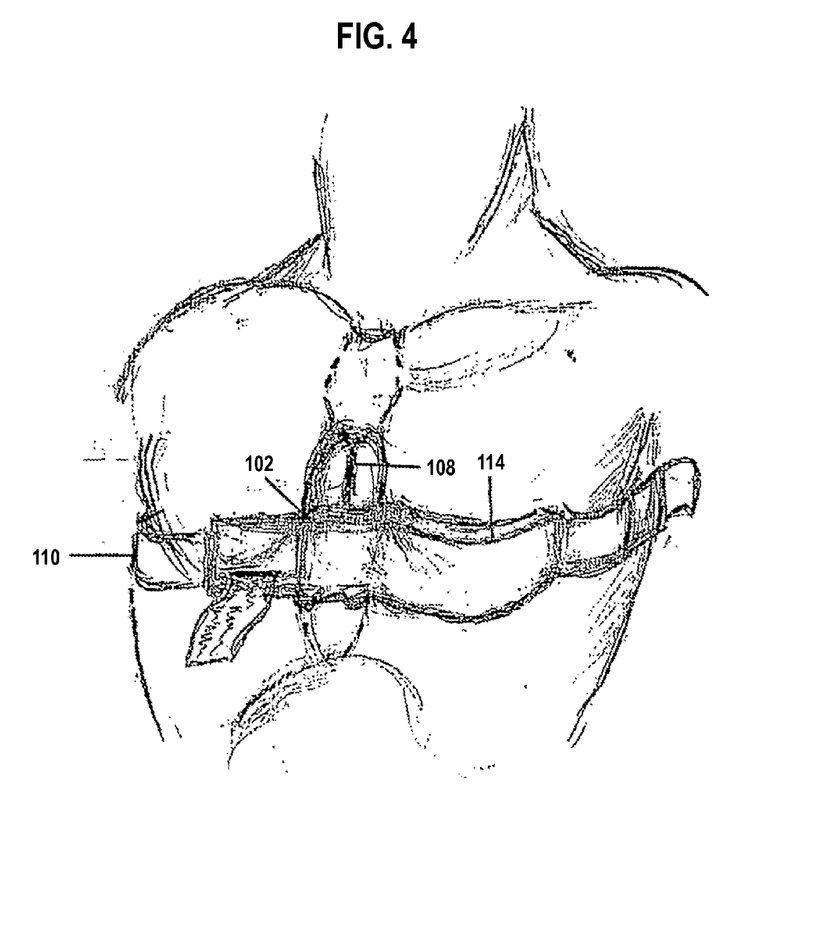
FIG. 4 is a view of an electrocardiogram device, according to the present invention, as worn on a patient's chest.

FIG. 3 shows a detailed view of a conductive gel pad 106 according to an embodiment of the present invention. The gel pad 106 is shaped like the first side of the housing 112. That is, it includes a straight lower edge for positioning adjacent the lower edge of the housing, and an upper edge with straight and curved portions for positioning adjacent the upper edge of the housing. The overall length of the gel pad 106 is approximately the same as the housing 102. The gel pad 106 also includes flaps 122 located at positions corresponding to the electrodes 104 on the housing 102. Each flap 122 includes a circular portion defining a gel disc 124 and a short arm portion defining a living hinge 126 that allows the disc to move with an electrode 104 when the gel pad 106 is coupled with the housing 102. Alternatively, the gel pad 106 can consist of a plurality of gel discs 124 on a strip of a carrier paper or other flexible carrier material. The choice of the paper or the material should be one that can withstand moisture due to perspiration from the patient. The gel pad 106 may be disposable or reusable. In one embodiment, the gel pad is made of an adhesive, disposable material. The gel pad is preferably made of an inexpensive paper or material if it is to be disposable. This embodiment is more cost-effective than conventional adhesive, disposable gel pads typically used with electrocardiogram devices because the electrodes are not embedded in the gel pad, so only the gel pad is disposed of after use. In another embodiment, the gel pad is made of a non-adhesive material that can be either disposable or reusable. A non-adhesive gel pad is held adjacent to the patient's chest in the proper position by means of pressure from the housing, the spring-loaded electrodes, and/or the securing mechanism. A non-adhesive, reusable gel pad can be cleaned and reused for multiple patients.

An elastic member disposed on the device places the gel pad in compression between the electrodes 104 and the patient's chest. Such compression ensures conductivity between the electrodes 104 and the patient's skin. The compression of the elastic member may be achieved by several means. As a first example, the elastic member may be composed of one or more springs disposed between the housing and one or more electrodes (e.g., springs disposed in the frustoconical collars). As a second example, the elastic member can also be part of the housing itself, such as when the housing is formed of an elastic member and attached to the patient's chest to create sufficient contact and compression. This effect can be achieved by the use of the attachment mechanism 110, described below, which creates the effect of an elastic member between the housing 102 and the body. A housing made of a flexible, non-rigid material is well-suited for use as the elastic member. As a third example, the elastic member can be comprised of the conductive gel pad 106. In particular, a gel that is sufficiently thick can act as a spring by adjusting based on compression between the electrodes 104 and the patient's chest to allow for good conductivity.

Electrode positioner 108 protrudes from a superior portion of the housing 102, along the patient's midline. The electrode positioner 108 is used to ensure accurate placement of the housing 102 over the patient's heart. In a preferred embodiment, the electrode positioner 108 is made of a semi-rigid material, such as urethane or rubber, to ensure that it does not press into the patient's flesh or cause discomfort, but other materials can be used, including rigid and flexible materials. The positioner 108 is preferably movable between two or more positions. In a first position, shown in FIG. 6 with broken lines, a distal tip of the electrode positioner 108 is disposed within the housing 102. This is useful, for example, for storage purposes to prevent damage when the electrode positioner is being transported or when it is not in use. In a second position, shown in FIG. 1, the electrode positioner 108 extends perpendicularly from the upper edge of the housing. Furthermore, in the second position, the electrode positioner 108 can preferably be extended to a plurality of extended positions to adjust for variations in patients' heights. The electrode positioner 108 can be movable by attaching a lower end thereof to the housing by means of a pivot joint 131, and configuring the lower end to be slotted with 133 so it can be linearly translatable relative to the pivot joint. Detents in the slot 133 can hold the positioner in a desired extended position. The distal tip of the electrode positioner 130 is at a second position when it is adjusted to a distance corresponding to a desired spacing between the electrodes 104 and the patient's jugular notch. When adjusted to the longest position, the electrode positioner 108 is fit for a tall patient, and the shortest position is for a patient of smaller stature, such as a child. The length of the electrode positioner 108 is preferably 2-4 inches. For example, the electrode positioner can be configured with three extended positions corresponding generally to children, females and males. Markings on the electrode positioner 132 may indicate the plurality of positions, so one can utilize the markings to determine an appropriate extended position for a particular body size. In one embodiment, at each position of the electrode positioner 108 is a small notch combined with a detent mechanism so that the electrode positioner can "click" into place at the desired position. Once the electrode positioner 108 has been adjusted to the appropriate position, the distal tip of the electrode positioner 130 should be placed at the patient's jugular notch. When the electrode positioner is aligned at the midline and with the jugular notch, the housing is accurately positioned over the patient's heart.

Once the proper position of the housing is determined, the housing is secured to the patient's body so that it will stay in place. An attachment mechanism 110, such as an adjustable or flexible belt, extends from one end of the housing, around the body, and attaches to the other end of the housing. In a preferred embodiment, the attachment mechanism 110 may resemble a seat belt, in which the distal end of the belt attaches to the opposite end of the housing by means of a buckle or a similar apparatus. The attachment mechanism 110 can include a release button 134 to release the attachment mechanism when the housing is to be removed from the patient's body. The attachment mechanism 110 may be retractable so that it is stored inside the housing 102 when not in use. The attachment mechanism 110 should be made adjustable or flexible so that it can be used on patients of varying size. This adjustable property can be achieved, for example, by use of an adjustment strap (like on a seat belt) or by use of a material with elastic properties.

Figure 6:
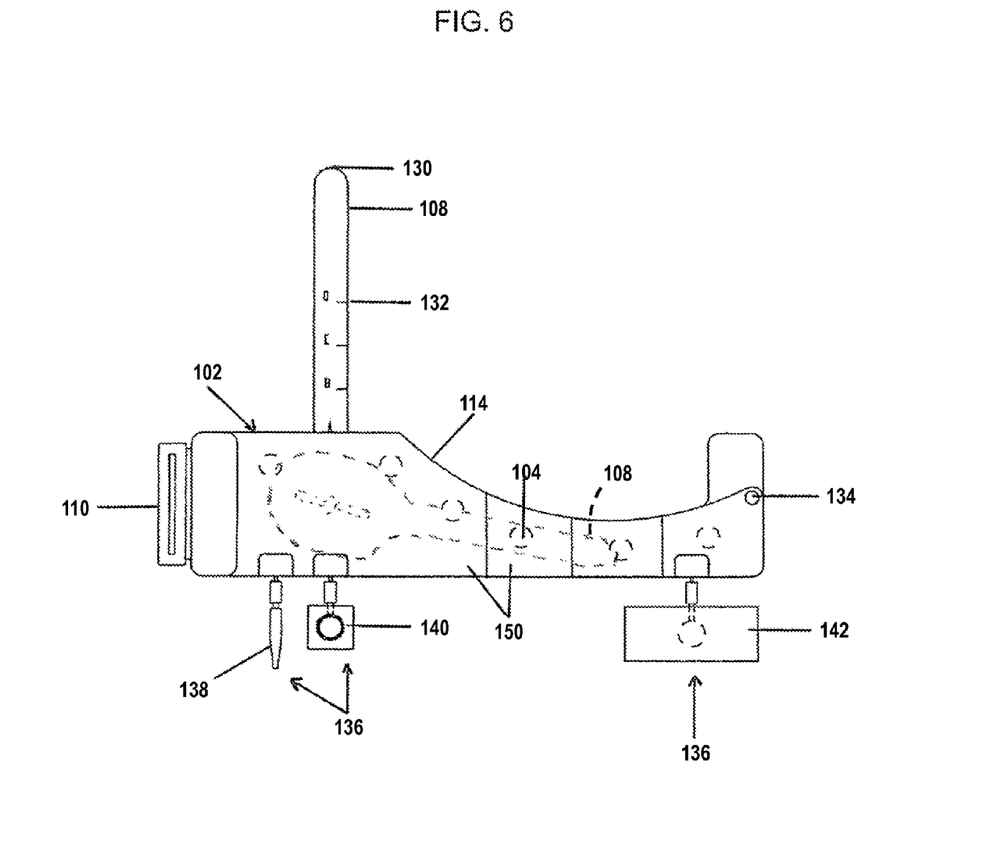
FIG. 6 is a top view of a segmented housing for an electrocardiogram device according to an embodiment of the present invention.

In addition to the precordial electrodes 104, the electrocardiogram preferably also contains a plurality of limb electrodes 136. The limb electrode wires are moveable between a retracted position and an extended position. In the retracted position, the limb electrode wires can be stored inside the housing, for example, on spring-loaded spools. This arrangement of the limb electrode wires helps avoid the problem of wires becoming tangled and protects the wires and/or electrodes from damage associated with transport or storage of the portable electrocardiogram device. Once the housing is positioned on the patient's body, the limb electrode wires are extended from the housing to the desired lengths. In a preferred embodiment, the retraction mechanism is similar to that of a tape measure. That is, the limb electrode wires are mounted on spring-loaded spools and are paired with a locking mechanism so that the wires may be set in a locked position after they have been retracted or extended to the desired lengths. When the locking mechanism is released, the wires automatically retract back into the housing. The limb electrodes 136 may be attached to the proper positions on the arms and leg by a variety of means. As shown in FIG. 6, the wires can terminate in alligator clips 138 or similar attachment means to be used in conjunction with a conventional adhesive gel pads with built-in electrodes. Referring still to FIG. 6, the wires can alternatively terminate in electrodes that snap onto adhesive gel pads 140. The adhesive gel pads, whether or not in combination with electrodes, may be either reusable or disposable. Another alternative method of attachment, also shown in FIG. 6, is electrode wires that terminate in electrodes attached to wrist or ankle straps 142. With a strap attachment 142, a gel pad, similar to that described above for use with the precordial electrodes, can be used for the limb electrodes 136. These wrist straps can be made of an adjustable or flexible material so that they can be used on patients of varying size. The electrodes of the strap attachments can be cleaned and reused on multiple patients.

Figure 5:
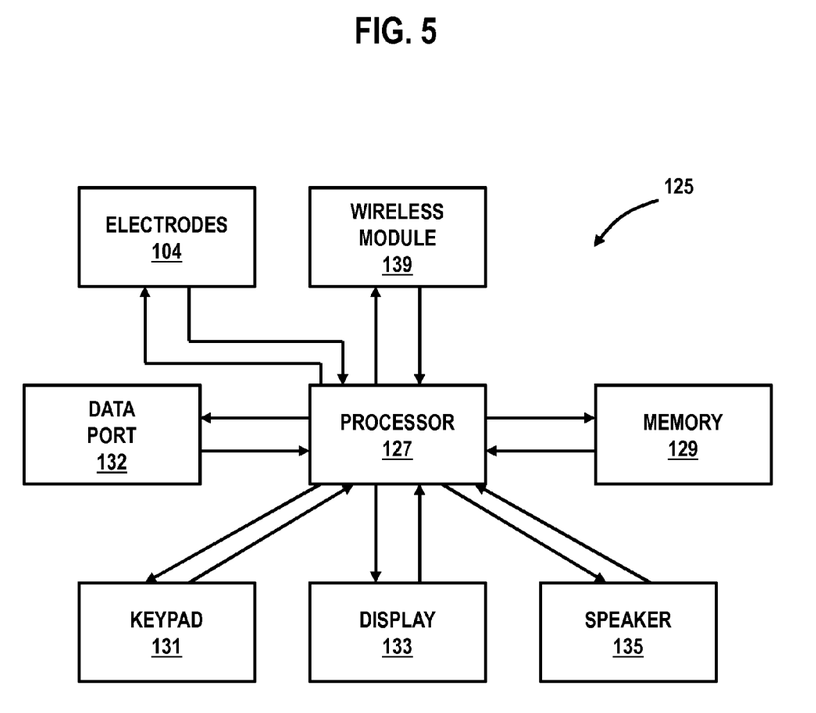
FIG. 5 is a schematic diagram of electronic components of an electrocardiogram device according to an embodiment of the present invention.

FIG. 5 is a schematic diagram of an electronic circuit 125 for an EKG device 100 according to the present invention. The circuit 125 includes one or more processors 127 capable of executing machine-readable instructions stored in memory 129. Circuit 125 may also include one or more of the following: a keypad 131, display 133, speaker 135, data port 137, and wireless communications module 139. In a basic embodiment, the memory 129 stores instructions which, when executed by the processor 127, cause the device 100 to automatically administer an electrocardiogram and obtain test results using electrodes 104. In an embodiment, the circuit 125 causes an electrocardiogram to be administered in response to an input entered on keypad 131, which preferably includes one or more buttons. Once the process of administering the electrocardiogram is completed, the circuit 125 preferably provides an audio indication via a speaker 135 and/or a visual indication via display 133. In an embodiment, electrocardiogram test results may be displayed using display 133. In an embodiment, data port 137 may be any kind of data port, such as a standard USB port, and preferably, the data port may be used to connect a printer, a portable digital assistant (PDA), a computer, or other peripheral device, to EKG device 100 so that, e.g., the test results may be printed, stored or otherwise transferred from the device 100 to the peripheral device for further analysis and/or storage. In an embodiment, wireless communications module 139 includes a transceiver and antenna configured to send and receive wireless communications regarding electrocardiogram test results using a suitable wireless protocol, including without limitation Blutooth and WiFi protocols, between the EKG device 100 and a remote device such as a computer, a PDA, or other wireless device. In a further embodiment, memory 129 stores instructions which, when executed by processor 127 causes operating instructions for the user to be played via the display 133 and/or speaker 135. In yet a further embodiment, the circuit 125 can be configured to present a graphical user interface on the display 133 that prompts a user how to operate the electrocardiogram device. In an embodiment, this interface can be achieved with a flat, touch screen panel LCD screen. The circuit 125 may also include an audio jack to enable the user to receive auditory instructions through use of ear buds or headphones.

The housing 102 can be a single enclosure as shown in FIGS. 1-5 or it can be a plurality of housing segments, as shown in FIG. 6. The housing segments 150 are connected via one or more flexible couplings that allow the housing to conform to the convexities of varying patients' chests. In one embodiment, the segments 150 are connected by a material with elastic properties so that the segments automatically adjust in relation to each other. In another embodiment, the segments 150 are connected by adjustable hinges. The expansion and contraction of gaps between the segments can be controlled by sliding the segments relative to the hinges, e.g., using knobs on the housing.

Referring to FIG. 2, it can be seen that the electrocardiogram device 100 may include a data port 152, such as a USB port, by which a data cable or telemetry module may be connected to the housing 102. A plug in accessory could lead to a printer, a Bluetooth, a telecommunications device, or another device that is desired to be connected to the electrocardiogram device 100. The electrocardiogram results can be communicated by a variety of methods. The electrocardiogram device 100 remotely conveys data to a health care professional for interpretation. The electrocardiogram records are coded by account name and stored off line at a highly secure data hosting facility, such as Dupont Fabros in Virginia. All data is immediately accessible for physician review with the ability to perform a baseline comparison that prompts the user if there is need for further action.

Auxiliary test functions can also be added to the electrocardiogram device 100. For example, the electrocardiogram device may be paired with other medical accessories or medical devices such as a blood pressure monitor, a heart rate monitor, a thermometer, a stethoscope, or a camera. The auxiliary functions can, similarly, be securely telecommunicated to a remotely located physician or diagnosing specialist, as described above.

To use the electrocardiogram device 100 of the present invention, the user (e.g., the patient, emergency personnel, or care giver) attaches the conductive gel pad 106 to the first side of the housing 112 by use of the attachment 110 means and lock mechanism 120. Once the conductive gel pad 106 is secured to the first side of the housing 112, the user holds the housing 102 in front of the left side of the patient's chest so that the electrode positioner 108 is at a top portion of the housing and the first side of the housing is against the patient's body. The user aligns the proximal edge of the housing 102 with the patient's midline. The user determines which marking on the electrode positioner 132 corresponds to his or her height, and extends the electrode positioner 108 to the determined marking. The user finds the patient's jugular notch, located at the base of the neck and at the superior border of the sternum, and aligns the distal tip of the electrode positioner 130 with the jugular notch. At this point, the housing should be accurately positioned over the patient's heart. The user then extends the attachment mechanism 110 from a first end of the housing 102, pulls the attachment mechanism 110 around the patient's body, and attaches the distal end of the attachment mechanism to the opposite end of the housing. The user extends each of the limb electrode wires from the housing 102 to the desired positions of the limbs as instructed by the patient's physician or laboratory technician. The user attaches the limb electrodes 136 to the desired positions on the patient's limbs (e.g., by use of adhesive gel pads or strap attachments). In a preferred embodiment, the user follows prompts from the graphical user interface of a handheld device to administer the electrocardiogram test. Upon completion of the test, the patient removes the limb electrodes 136 and releases the locking mechanisms of the limb electrode wires so that they retract back inside the housing 102 for storage. The user then presses the release button 134 to remove the attachment mechanism 110 from its secure position around the body so that the attachment mechanism retracts inside the housing for storage. The user removes the housing 102 from the patient's chest and returns the electrode positioner 108 to a first position for storage.

While the invention has been particularly taught and described with reference to certain preferred embodiments, those versed in the art will appreciate that modifications in form and detail may be made without departing from the spirit and scope of the invention. For example, while the device housing has been shown as having a contoured side facing the patient and a flat side facing outwardly, it will be appreciated that either or both sides can be partly or fully contoured. Similarly, the housing may be configured to have a pectoral cut-away along an upper edge as shown or be configured to extent partly or fully across the chest without a cut-away portion. The attachment mechanism may include straps that are detachable from the housing, fixed to opposite ends of the housing, or formed integrally as part of the housing. All such modifications are intended to fall within the scope of the appended claims.

The invention claimed is:

1. An electrocardiogram device comprising:
 a reusable housing enclosure with a first side configured for placement adjacent a chest of a patient;
 a plurality of electrodes fixed on said first side of said housing enclosure at locations that align with precordial positions on a chest of a patient;
 a disposable conductive gel pad detachably coupled to said housing enclosure and extending over two or more of said plurality of electrodes on said first side so as to be disposed between said two or more electrodes and the chest of a patient when the electrocardiogram device is attached to the patient; and
 an attachment mechanism extending from said housing enclosure for holding the housing enclosure correctly in place on the chest of a patient; and
 further comprising an elastic member disposed on said housing enclosure to place said gel pad in compression between said electrodes and the chest of the patient.

2. An electrocardiogram device according to claim 1, wherein said gel pad is said elastic member.

3. An electrocardiogram device according to claim 1, wherein said gel pad is formed of a non-adhesive material.

4. An electrocardiogram device comprising:
 a housing with a first side configured for placement adjacent a chest of a patient;

a plurality of electrodes fixed on said first side of said housing at locations that align with precordial positions on a chest of a patient;
a disposable conductive gel pad detachably coupled to said housing and extending over two or more of said plurality of electrodes on said first side so as to be disposed between said two or more electrodes and the chest of a patient when the electrocardiogram device is attached to the patient;
an attachment mechanism extending from said housing for holding the housing correctly in place on the chest of a patient; and
an elastic member disposed on said housing to place said gel pad in compression between said electrodes and the chest of the patient;
wherein said elastic member is a spring disposed between said housing and an electrode.

5. An electrocardiogram device comprising:
a housing with a first side configured for placement adjacent a chest of a patient;
a plurality of electrodes fixed on said first side of said housing at locations that align with precordial positions on a chest of a patient;
a disposable conductive gel pad detachably coupled to said housing and extending over two or more of said plurality of electrodes on said first side so as to be disposed between said two or more electrodes and the chest of a patient when the electrocardiogram device is attached to the patient;
an attachment mechanism extending from said housing for holding the housing correctly in place on the chest of a patient; and
an elastic member disposed on said housing to place said gel pad in compression between said electrodes and the chest of the patient;
wherein said elastic member is at least part of said housing.

6. An electrocardiogram device comprising:
a housing with a first side configured for placement adjacent a chest of a patient;
a plurality of electrodes fixed on said first side of said housing at locations that align with precordial positions on a chest of a patient;
a disposable conductive gel pad detachably coupled to said housing and extending over two or more of said plurality of electrodes on said first side so as to be disposed between said two or more electrodes and the chest of a patient when the electrocardiogram device is attached to the patient; and an attachment mechanism extending from said housing for holding the housing correctly in place on the chest of a patient;
wherein a pair of openings are formed at opposite ends of said housing and wherein said gel pad includes tab portions configured to be received within said openings.

7. An electrocardiogram device according to claim 6, wherein said housing further includes a lock mechanism at each of said openings with a movable member configured to retain said tab portions of said gel pad in said openings in a locked position and to permit removal of said tab portions from said openings in an unlocked position.

8. An electrocardiogram device comprising:
a housing with a first side configured for placement adjacent a chest of a patient;
a plurality of electrodes fixed on said first side of said housing at locations that align with precordial positions on a chest of a patient;
a disposable conductive gel pad detachably coupled to said housing and extending over two or more of said plurality of electrodes on said first side so as to be disposed between said two or more electrodes and the chest of a patient when the electrocardiogram device is attached to the patient; and
an attachment mechanism extending from said housing for holding the housing correctly in place on the chest of a patient;
wherein said gel pad includes flaps located at positions corresponding to electrodes on said housing when said gel pad is attached to said housing.

9. An electrocardiogram device comprising:
a reusable housing enclosure with a first side configured for placement adjacent a chest of a patient;
a plurality of electrodes fixed on said first side of said housing enclosure at locations that align with precordial positions on a chest of a patient;
a disposable conductive gel pad detachably coupled to said housing enclosure and extending over two or more of said plurality of electrodes on said first side so as to be disposed between said two or more electrodes and the chest of a patient when the electrocardiogram device is attached to the patient; and
an attachment mechanism extending from said housing enclosure for holding the housing enclosure correctly in place on the chest of a patient; and
further comprising a plurality of limb electrode wires connected to said housing enclosure and movable between a retracted position and an extended position.

10. An electrocardiogram device according to claim 9, wherein said limb electrode wires are lockable in at least one of the retracted and extended positions.

11. An electrocardiogram device comprising:
a reusable housing enclosure with a first side configured for placement adjacent a chest of a patient;
a plurality of electrodes fixed on said first side of said housing enclosure at locations that align with precordial positions on a chest of a patient;
a disposable conductive gel pad detachably coupled to said housing enclosure and extending over two or more of said plurality of electrodes on said first side so as to be disposed between said two or more electrodes and the chest of a patient when the electrocardiogram device is attached to the patient; and
an attachment mechanism extending from said housing enclosure for holding the housing enclosure correctly in place on the chest of a patient; and
wherein said housing enclosure includes a plurality of segments connected via one or more flexible couplings.

12. An electrocardiogram device comprising:
a reusable housing enclosure with a first side configured for placement adjacent a chest of a patient;
a plurality of electrodes fixed on said first side of said housing enclosure at locations that align with precordial positions on a chest of a patient;
a disposable conductive gel pad detachably coupled to said housing enclosure and extending over two or more of said plurality of electrodes on said first side so as to be disposed between said two or more electrodes and the chest of a patient when the electrocardiogram device is attached to the patient; and
an attachment mechanism extending from said housing enclosure for holding the housing enclosure correctly in place on the chest of a patient; and
further comprising a power supply, a processor and a memory disposed within said housing enclosure, said memory storing computer-readable instructions executable by said processor to cause the electrocardiogram device to operate.

13. An electrocardiogram device according to claim 12, further comprising a wireless communication module in said housing enclosure for receiving electrocardiogram test results from said processor and transmitting said electrocardiogram test results to a remote device.

14. An electrocardiogram device according to claim 12, wherein said stored instructions include at least one of audio and visual data describing proper use of said electrocardiogram device.

15. An electrocardiogram device comprising:
  a housing with a first side configured for placement adjacent a chest of a patient;
  a plurality of electrodes fixed on said first side of said housing at locations that align with electrocardiogram positions on the chest of a patient;
  an electrode positioner having a distal tip extendible from a first position relative to said housing to a second position spaced from said housing, said distal tip being spaced from said housing in said second position a distance corresponding to a desired spacing between said electrodes and a jugular notch of the patient; and
  an attachment mechanism for attaching the housing on the chest of the patient;
  wherein said distal tip is disposed within said housing in said first position.

16. An electrocardiogram device comprising:
  a housing with a first side configured for placement adjacent a chest of a patient;
  a plurality of electrodes fixed on said first side of said housing at locations that align with electrocardiogram positions on the chest of a patient;
  an electrode positioner having a distal tip extendible from a first position relative to said housing to a second position spaced from said housing, said distal tip being spaced from said housing in said second position a distance corresponding to a desired spacing between said electrodes and a jugular notch of the patient; and
  an attachment mechanism for attaching the housing on the chest of the patient;
  wherein said electrode positioner is attached to said housing at a pivot joint.

17. An electrocardiogram device according to claim 16, wherein said electrode positioner is linearly translatable relative to said pivot joint.

18. An electrocardiogram device according to claim 17, wherein said electrode positioner includes markings along its length at different positions corresponding to desired spacings between said electrodes and the jugular notches of patients of different body sizes.

19. A method of administering an electrocardiogram comprising the steps of:
  attaching to a reusable housing enclosure having electrodes fixed thereon a disposable conductive gel pad to cover the fixed electrodes;
  positioning the housing enclosure adjacent a chest of a patient so that at least some of the electrodes are aligned with precordial positions and the gel pad is disposed between the housing enclosure and the patient;
  securing the housing enclosure to the patient such that the gel pad is placed in compression between the housing enclosure and the chest of the patient;
  administering an electrocardiogram using the housing enclosure and the gel pad; and
  removing the gel pad from the housing enclosure.

20. A method of administering an electrocardiogram according to claim 19, further comprising the step of extending at least one electrode wire from the housing enclosure to at least one of the patient's limbs.

21. A method of administering an electrocardiogram comprising the steps of:
  attaching to a housing having electrodes fixed thereon a disposable conductive gel pad to cover the fixed electrodes;
  positioning the housing adjacent a chest of a patient so that at least some of the electrodes are aligned with precordial positions and the gel pad is disposed between the housing and the patient;
  securing the housing to the patient such that the gel pad is placed in compression between the housing and the chest of the patient;
  administering an electrocardiogram using the housing and the gel pad; and
  removing the gel pad from the housing;
  wherein said attaching step includes locking ends of the gel pad in openings formed at opposite ends of the housing and said removing step includes unlocking ends of the gel pad so they can be removed from the openings.

* * * * *